(12) United States Patent
Rosenqvist et al.

(10) Patent No.: US 6,440,311 B1
(45) Date of Patent: Aug. 27, 2002

(54) SYSTEM AND METHOD FOR MONITORING A DOSAGE PUMP IN A DIALYSIS MACHINE

(75) Inventors: Anders Rosenqvist, Lund; Erik Linderup, Bjärred, both of (SE)

(73) Assignee: Gambro AB (SE)

( * ) Notice: Subject to any disclaimer, the term of this patent is extended or adjusted under 35 U.S.C. 154(b) by 0 days.

(21) Appl. No.: 09/581,618

(22) PCT Filed: Dec. 14, 1998

(86) PCT No.: PCT/SE98/02297

§ 371 (c)(1),
(2), (4) Date: Jul. 14, 2000

(87) PCT Pub. No.: WO99/30756

PCT Pub. Date: Jun. 24, 1999

(30) Foreign Application Priority Data

Dec. 16, 1997 (SE) ............................................... 9704687

(51) Int. Cl.⁷ ......................... B01D 61/32; B01D 61/28
(52) U.S. Cl. ......................... 210/744; 210/85; 210/86; 210/97; 210/104; 210/134; 210/143; 210/258; 210/645; 210/646; 210/739; 222/64; 222/255
(58) Field of Search ............................ 210/85, 86, 104, 210/97, 134, 143, 258, 739, 744, 645, 646; 222/64, 638, 644, 23, 52, 63, 255

(56) References Cited

U.S. PATENT DOCUMENTS

| 4,137,168 A | 1/1979 | Perrot ........................... 210/96 |
| 4,319,568 A | * 3/1982 | Tregoning ................... 417/477 |

FOREIGN PATENT DOCUMENTS

| DE | 41 27 675 A1 | 2/1993 |
| EP | 0 278 100 A2 | 8/1988 |
| EP | 0 536 645 A2 | 4/1993 |

* cited by examiner

*Primary Examiner*—John Kim
(74) *Attorney, Agent, or Firm*—Lerner, David, Littenberg, Krumholz & Mentlik, LLP

(57) ABSTRACT

Apparatus is disclosed for monitoring the flow of a fluid through a dosage pump in a dialyzer including an auxiliary pump disposed between a fluid source for the dosage pump and the dosage pump itself, a slave chamber between the auxiliary pump and the dosage pump, the slave chamber including a level detector for detecting a predetermined level of the fluid in the salve chamber and emitting a signal when the level of the fluid is below the predetermined level, and a controller for activating the auxiliary pump after the level indicator emits the signal such that the slave chamber is refilled with the fluid by the auxiliary pump after the suction stroke of the dosage pump has drawn the fluid into the dosage pump and caused the level indicator to emit the signal. Methods for monitoring the flow of a fluid through the dosage pump are also disclosed.

13 Claims, 3 Drawing Sheets

SYSTEM AND METHOD FOR MONITORING A DOSAGE PUMP IN A DIALYSIS MACHINE

FIELD OF THE INVENTION

The present invention relates to a method for monitoring a dosage pump intended for pumping a concentrate to be diluted in water. More particularly, the present invention relates to a monitoring system for a dosage pump for pumping a concentrate fluid at a very low flow rate, preferably in connection with a dialysis machine.

BACKGROUND OF THE INVENTION

European Patent Application No. 278,100 describes a dialysis machine in which the present invention may be utilized. That dialysis machine comprises a preparation unit for a dialysis fluid in which preparation of the dialysis fluid takes place on-line, starting from concentrates in powder form located in separate cartridges.

Normally, a dialysis machine comprises two portions, a first blood handling portion for feedings blood from a patient through an extracorporeal fluid circuit comprising a dialyzer, and a second dialysis fluid handling portion for preparing a dialysis fluid and transporting it through the dialyzer, and then to a drain. The dialyzer comprises a semi-permeable membrane separating the dialyzer into a blood containing portion and a dialysis fluid containing portion. Transport of molecules, ions, substances and water takes place across the membrane for conditioning the blood to replace the function of the kidneys.

The dialysis fluid normally has a composition which substantially matches that of the patient's blood plasma, with certain modifications. In addition to water, a dialysis fluid normally comprises the following substances in ionic form: sodium, bicarbonate, potassium, magnesium, calcium, chloride and acetate. The pH value of the fluid is adjusted to between about 7.1 and 7.4. In addition, the fluid may comprise glucose and other substances.

Two ions are present in large quantities in the dialysis fluid, namely sodium and bicarbonate.

European Patent Application No. 278,100 describes the preparation of a dialysis fluid in which these two ions are obtained on-line from powder cartridges containing sodium bicarbonate and sodium chloride, respectively, in the form of a dry powder or granules. Water is passed through the cartridges and substantially saturated fluids of sodium bicarbonate and sodium chloride, respectively, exit the cartridges. Two dosage pumps ensure that the correct quantity of concentrate fluid is fed to a main conduit comprising clean water obtained from a reverse osmosis unit.

The dialysis fluid normally comprises about 35 mmol/l of bicarbonate and about 140 mmol/l of sodium. In total, about 120 liters of dialysis fluid is consumed during one treatment, which normally lasts for four hours and takes place three times a week.

Furthermore, the dialysis fluid contains magnesium, potassium, calcium, acetic acid and glucose in suitable quantities. In the dialysis machine according to European Patent Application No. 278,100, these other components are obtained from an ionic bag. Since these substances have a relatively low concentration in the prepared dialysis fluid, the contents of the ionic bag can be very concentrated, in the ratio of about 1:200 to 1:500, whereby the volume of the bag is small, about ½ liter.

The dosing of the contents of the ionic bag is performed using a dosage pump. The dosage pump feeds the contents of the ionic bag to the main conduit in the dialysis machine with a flow rate of about 1 ml/min.

A dialysis machine further comprises a supervisory system which supervises or monitors vital operations of the dialysis machine. A malfunction of such vital operations could result in the patient not obtaining adequate treatment, becoming ill, or being harmed or even dying.

One operation which must be monitored is the dosage pump of the ionic bag. Too high a dosage of the contents in the ionic bag could lead to heart failure, while too low a dosage could lead to other symptoms.

It is not simple to monitor such a low flow rate as that which passes from the ionic bag; i.e., the order of about 1 ml/min. A large deviation must be able to be noted quickly enough for suitable corrective measures to be undertaken, at least within one minute, and preferably within ten seconds. The accuracy must be high and at least within the range of about +/−5%.

The contents of the ionic bag comprise salts having a high ionic strength. Mechanical flow measurement devices run the risk of jamming if salt crystals are precipitated, for which there is a great risk.

It is previously known to measure such small flows using thermal flow sensors (see, for example, German Patent Application No. 4,127,675). These sensors are, however, greatly influenced by a change in the ambient temperature, and false alarms may easily be emitted. A dialysis machine must operate equally well at temperatures of about 20° C., as well as at ambient temperatures of 35° C., which may be the case in certain countries. In addition, large temperature differences and temperature changes arise internally in a dialysis machine, for example during and shortly after heat sterilisation, which may also lead to problems. In certain cases, a thermal flow detector must be calibrated for different types of fluids because of different densities and heat capacities dependent on the concentration of the constituent substances.

One object of the present invention is to provide a system and a method for monitoring a dosage pump intended for low flow rates, in the order of about 1 ml/min, which is accurate and able to trigger an alarm signal within a reasonable time.

A further object of the present invention is to provide a monitoring system for a dosage pump for low flow rates which is sturdy, and scarcely affected by the surroundings, such as ambient temperatures.

SUMMARY OF THE INVENTION

In accordance with the present invention, these and other objects have now been realized by the invention of apparatus for monitoring the flow of a fluid through a dosage pump having a suction stroke for drawing the fluid into the dosage pump from a source of the fluid and a discharge stroke for discharging the fluid from the dosage pump, the apparatus comprising an auxiliary pump disposed between the fluid source and the dosage pump, a slave chamber disposed between the auxiliary pump and the dosage pump, the slave chamber including a level detector for detecting a first predetermined level of the fluid in the slave chamber and emitting a signal when the level of the fluid in the slave chamber is below the first predetermined level, and control means for activating the auxiliary pump after the level detector emits the signal whereby the slave chamber is refilled with the fluid by the auxiliary pump after the suction stroke of the dosage pump has drawn the fluid into the dosage pump and caused the level indicator to emit the signal. In a preferred embodiment, the dosage pump is incorporated in a dialyzer.

In accordance with one embodiment of the apparatus of the present invention, the control means is adapted to activate the auxiliary pump to refill the slave chamber to a second predetermined level above the first predetermined level of the fluid in the slave chamber.

In accordance with another embodiment of the apparatus of the present invention, the apparatus includes regulating means for regulating the dosage pump whereby the suction stroke is carried out at a first speed and the discharge stroke is carried out at a second speed, the first speed being substantially greater than the second speed and the second speed providing a substantially constant flow rate.

In accordance with another embodiment of the apparatus of the present invention, the auxiliary pump includes measuring means for measuring the volume of the fluid pumped by the auxiliary pump during each cycle thereof, the control means including time measuring means for measuring the time between each cycle of the auxiliary pump and calculating means for calculating the flow of the fluid through the dosage pump based on the ratio between the volume of the fluid measured by the measuring means and the time between each of the cycles of the auxiliary pump measured by the time measuring means.

In accordance with another embodiment of the apparatus of the present invention, the auxiliary pump comprises a second dosage pump having a predetermined volume per cycle or portion thereof, and wherein the slave chamber includes a side wall and an outlet for the second dosage pump, the inlet being disposed adjacent to the side wall of the slave chamber.

In accordance with the present invention, a method has also been devised for monitoring the flow of a fluid through a dosage pump having a suction stroke for drawing the fluid into the dosage pump from a source of the fluid and a discharge stroke for discharging the fluid from the dosage pump, an auxiliary pump disposed between the source of the fluid and the dosage pump, and a slave chamber disposed between the auxiliary pump and the dosage pump, the method comprising detecting the level of the fluid in the slave chamber and emitting a signal when the level is below a first predetermined level in the slave chamber, and actuating the auxiliary pump after emitting the signal whereby the level of the fluid in the slave chamber is increased above a second predetermined level by the discharge stroke of the dosage pump. In a preferred embodiment, the dosage pump is incorporated in a dialyzer.

In accordance with one embodiment of the method of the present invention, the second predetermined level is greater than the first predetermined level, whereby the slave chamber is topped up with a predetermined hysteresis value above the first predetermined level.

In accordance with another embodiment of the method of the present invention, the method includes activating the auxiliary pump with a predetermined time delay after emitting the signal.

In accordance with another embodiment of the method of the present invention, the method includes regulating the dosage pump so that the suction stroke is carried out at a first speed and the discharge stroke is carried out at a second speed, the first speed being substantially greater than the second speed, and the second speed providing a substantially constant flow rate.

In accordance with another embodiment of the method of the present invention, the method includes measuring the volume of the fluid flowing through the auxiliary pump for each cycle thereof, measuring the time between each cycle of the auxiliary pump, and calculating the fluid flow through the dosage pump by determining the ratio between the measured volume of the fluid flowing through the auxiliary pump and the measured time between each cycle of the auxiliary pump.

According to the present invention, the above objects are achieved by a method and a system for monitoring a dosage pump, particularly in a dialysis machine, in which the dosage pump has a suction stroke for drawing a fluid into the dosage pump from a source of the fluid, and a discharge stroke for discharging the fluid from the dosage pump. The system includes a second pump arranged between the source of the fluid and the dosage pump, a slave chamber arranged between the dosage pump and the second pump, a level detector arranged in the slave chamber for emitting a signal when the level of the fluid in the slave chamber is below the level of the level detector, and a control arrangement for activating the second pump when the level detector emits a signal during and/or after a suction stroke of the dosage pump for refilling the slave chamber to a predetermined level before initiation of the next suction stroke.

Preferably, the control arrangement according to the present invention is arranged to fill the slave chamber with a predetermined volume above the level of the level detector. Moreover, there is preferably a regulating arrangement for regulating the dosage pump for obtaining a fast suction stroke and a regulated discharge stroke in which the discharge fluid flow rate is substantially constant.

In accordance with one embodiment of the present invention, the second pump comprises a measuring arrangement for measuring the volume of fluid passing through the second pump for each cycle, whereby the control arrangement comprises a time measurement device for measuring the time between successive cycles, and a calculation arrangement for calculating the fluid flow rate through the dosage pump by determining the ratio between said volume measurement and said time measurement.

Preferably, the second pump is a dosage pump with a known volume per revolution, or per partial revolution or the like, and the slave chamber consists of a chamber with an inlet from the second pump, which inlet is arranged immediately adjacent the side wall of the chamber.

BRIEF DESCRIPTION OF THE DRAWINGS

The present invention will be more fully appreciated with reference to the following detailed description, which, in turn, refers to the drawings in which.

DETAILED DESCRIPTION OF THE INVENTION

The present invention is described below in greater details with reference to a preferred embodiment which is intended for use in a dialysis machine, in particular, a GAMBRO AK 200, which is sold by GAMBRO AB of Sweden. The principles underlying the present invention may be employed in other types of dialysis machines with modifications which will be readily apparent to skilled persons in the art.

Figure 1:
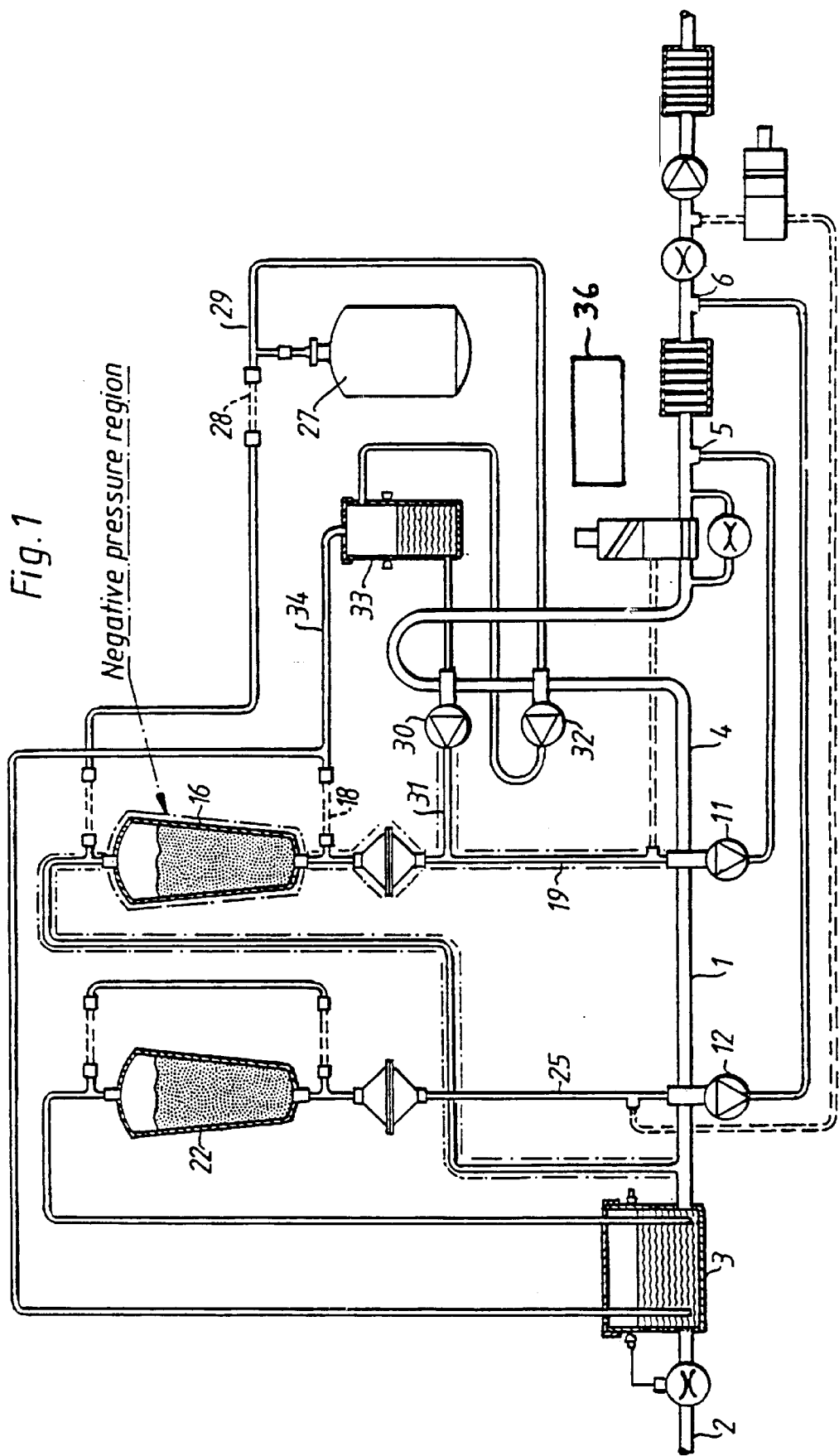
FIG. 1 is a schematic diagram of a dialysis fluid preparation portion of a dialysis machine provided with a monitoring system according to the present invention.

A flow diagram is shown in FIG. 1 for the above-mentioned dialysis machine in which only that part of the equipment is shown which is relevant to the present invention, namely the part in which preparation of the dialysis fluid takes place.

The dialysis machine is connected to an outlet for pure water which is normally available in a dialysis clinic. The water normally comes from an RO-unit (reverse osmosis unit) and is substantially free of ions and other impurities.

The water enters a main conduit 1 in the dialysis machine according to FIG. 1 through an inlet conduit 2. The inlet conduit 2 opens into a water reservoir 3, in which the water is heated to the appropriate temperature for use, which is normally about 37° C.

During a normal dialysis treatment, which lasts for about four hours, about 120 liters of water are used. Thus, it is necessary that ½ liter of dialysis fluid be prepared per minute (500 ml/minute). Other dialysis fluid flow rates may be used, though they normally lie in the region of about 300 to 700 ml/minute.

The water from the water reservoir 3 flows along a conduit 4 and reaches a first dosage point 5 where a first concentrate is added to the main flow, normally an A-concentrate. In addition, a second dosage point 6 is provided where a B-concentrate is added. A first dosage pump 11 is connected to the first dosage point 5 and a second dosage pump 12 is connected to the second dosage point 6.

The dosage pumps, 11 and 12, are connected to sources for concentrates through conduits, 19 and 25. In the shown embodiment, cartridges are used containing sodium chloride powder 16 and sodium bicarbonate powder 22. Water passes through the powder beds and forms concentrates of these substances.

In addition, a small bag 27 is provided, hereinafter called an ionic bag, which comprises about ½ liter of fluid with the remaining constituents which are not provided from the powder cartridges. The ionic bag 27 is arranged in a holder 28. A conduit 29 leads from the ionic bag to a third concentrate pump or dosage pump 30. The dosage pump 30 pumps the contents from the ionic bag through a conduit 31 which opens into the conduit 19.

The dosage pump 30 pumps the fluid in the ionic bag at a rate which is determined by the computer equipment of the dialysis machine. Normally, the dosage pump 30 is a so-called ceramic pump of the piston type. During a suction stroke, suction of fluid into the pump chamber of the pump takes place. During a discharge stroke, discharge of the fluid takes place, whereby the dosage pump is operated so that the suction stroke is as short as possible and the discharge stroke is dimensioned so that the discharged flow rate is relatively constant. The pump is driven by a step motor by means of a computer 36 in which the above-mentioned functions are programmed.

The monitoring of the dosage pump 30 takes place according to the present invention by means of an identical or similar second pump 32 and an intermediate slave chamber 33 which are located in the conduit 29 from the ionic bag to the dosage pump 30, as is shown in FIG. 1.

The fluid from the ionic bag 27 passes through the conduit 29 to the second pump 32 and further to the slave chamber 33 and to the dosage pump 30. As is apparent from FIG. 1, the upper end of the slave chamber is connected by a conduit 34 to the atmosphere by means of a connection 18 for the purpose of deaeration. In this manner, any air bubbles in the fluid from the ionic bag are separated out before dosage, which results in the dosage pump performing better.

The monitoring arrangement functions as follows. The dosage pump 30 is driven by a step motor which is controlled by the computer 36. The computer 36 is programmed to drive the step motor and the dosage pump 30 during the discharge stroke, during the first 180 degrees of rotation of the step motor, with a speed which results in the flow rate after the dosage pump being substantially constant, which means that the angular velocity of the step motor is high in the beginning and at termination of the half revolution, and is slow in the middle of the half revolution.

A suction stroke then takes place, in which liquid is fed to the dosage pump from the slave chamber. This suction stroke takes place as quickly as possible, which means that the step motor is driven with high speed during the second half revolution. This high speed is limited by such conditions as back pressure, viscosity of the liquid, etc. If the speed is too great, there is a risk that the pump chamber of the dosage pump is not completely filled during a suction stroke. If the speed is too low, the period of interruption in the flow from the dosage pump becomes too long.

Figure 2:
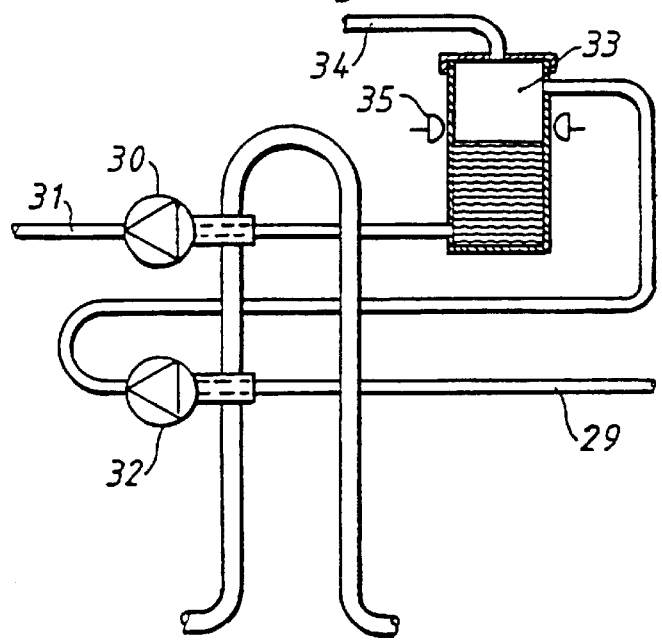
FIG. 2 is a top, elevational view of two pumps and an intermediate slave chamber in the monitoring system according to FIG. 1.

The slave chamber 33 is provided with a level detector 35, as is more clearly apparent from FIG. 2. During the suction stroke to the dosage pump, the level in the slave chamber drops below the level detector 35 and this emits a signal. The signal activates the second pump 32 which starts to pump liquid to the slave chamber from the ionic bag 27. The relationship between the flow from the slave chamber to the dosage pump during its suction stroke and the flow to the slave chamber from the second pump is such that the level in the slave chamber never reaches above the level detector. This normally means that the flow to the dosage pump is always greater than the flow from the second pump to the slave chamber, if both pumps are driven simultaneously.

When the suction stroke to the dosage pump is terminated, i.e. when the step motor has rotated from 180 degrees to 360 degrees, the flow from the slave chamber to the dosage pump becomes zero. Since the level detector 35 still emits a signal, the second pump continues to be driven until the level in the slave chamber reaches the level detector. Thereafter, the second pump 32 is driven for a further short period until a predetermined volume of liquid has been pumped to the slave chamber. The level in the slave chamber thus rises by a predetermined volume above the level detector. In this manner, a hysteresis is obtained in the signal of the level detector.

By means of this arrangement of the second pump and the slave chamber, the flow through the dosage pump 30 can be monitored. The flow through the second pump is known since this second pump is also a dosage pump, for example of the same type as the dosage pump 30. The time for each cycle can be obtained from the electrical signal from the level detector. The flow is thus the ratio between the pump volume and the cycle time.

The conditions which are to be monitored are, among others, the following:
1) that the flow from the dosage pump to the conduit 19 is always within certain error tolerance limits, such as +/−5%;
2) that no leakage is present in the conduits so that the dosage pump does not pump air;

3) that no cavitation takes place during the suction stroke to the dosage pump, which would result in a reduction of the displacement of the dosage pump, or that the dosage pump does not suffer a mechanical or electrical malfunction;

4) that an individual fault in the circuit from the ionic bag 29 to the input conduit 31 is detected, such as if no ionic bag is connected, the ionic bag is empty, there is a blockage, either completely or partially, or a small hole or a leakage in the ionic bag, the connection or the tubes;

5) that there is a fault in the operation of the second pump, such as that it operates at the wrong speed, misses steps or rotates in the wrong direction;

6) that there is a fault in the slave chamber, such as blockage or leakage in the slave chamber or in the deaeration conduit; and/or 7) that there is a fault in the level detector, such as constantly high, low, inverted or oscillating signal.

By employing a slave chamber, it is ensured that a condition in which only air passes through the dosage pump is detectable, resulting in the fact that no signal is obtained from the level detector.

By using a second pump in which the flow to the slave chamber may be monitored and measured completely independently of the operating function of the dosage pump, the dosage pump may be monitored so that it is within the stated range of +/-5%, or in the desired range.

If a malfunction arises, such as that a leakage arises in the conduit between the slave chamber and the dosage pump such that the dosage pump draws in air, this malfunction is detected within a stroke of the dosage pump due to the level detector not emitting a signal.

If a sudden change takes place in the delivery speed of the dosage pump, for example due to dramatically increased back pressure in the conduit 31, an indication from the second pump is obtained which, during the next stroke, pumps considerably less liquid or, alternatively, the time signal for the level detector becomes different.

The monitoring arrangement comprising the second pump and the level detector is operated according to a particular algorithm.

The algorithm for the monitoring arrangement not only monitors the volume which is pumped by the second pump 32, but it also relates this volume to a suitable time interval.

By relating the volume pumped by the second pump 32 to a period of the dosage pump 30, a stable and correct estimation with regard to the expectation value of the flow through the dosage pump is obtained.

The dosage pump 30 has a stable period, typically +/-200 ms at a period of about 11 seconds.

A cycle of the complex system of the dosage pump 30, the second pump 32 and the slave chamber 33 can be described as follows:

When the dosage pump 30 initiates its suction period, the level in the slave chamber 33 drops quickly from a well determined level above the level of the level detector.

After a short but stable delay from the dosage pump 30 initiating its suction stroke, the liquid level in the slave chamber 33 passes the level detector 35. When this is registered by the detector, the monitoring computer 36 terminates the time determination of the previous cycle of the dosage pump 30 and commences the next cycle. Since the delay is stable and does not vary to any great extent from one cycle to the other, the resulting time determination will provide a stable result.

The monitoring computer 36 thereafter introduces a time delay during which it calculates a flow rate estimation based on estimations of the preceding period's pumped volume and period time. Thereafter, the monitoring computer 36 starts refilling the slave chamber 33. This delay does not affect the performance of the system as long as refilling is completed before the next suction stroke is initiated.

In the meantime, the dosage pump 30 has continued its suction stroke. When the second pump 32 starts to pump, this takes place at a flow rate which is lower than that which the dosage pump 30 has during its suction period. Thus, the level in the slave chamber 33 will be a monotonously diminishing function of time. There is thus no way in which the level in the slave chamber during the suction stroke of the dosage pump can cross the detector 35.

The second pump 32 continues to fill the slave chamber 33 and, when the dosage pump 30 changes from suction stroke to discharge stroke, the level in the chamber rises.

When the level passes the level of the detector, the detector emits a signal and the monitoring computer 36 reacts by calculating how much longer filling should continue. Should the detector emit a plurality of closely spaced signals, the monitoring computer 36 will perform a new calculation of the continued filling time for each new signal. Thus, the filling time will be resistant to possible interference due to a plurality of successive signals from the level detector. If the second pump 32 is a ceramic dosage pump with a step motor, the calculation of continued filling time will depend on where on the rotation the detector signal is received. The continued filling takes place in order to achieve a constant, predetermined hysteresis volume above the switching level of the sensor. The hysteresis volume reduces the risk of false detector signals.

When the hysteresis volume is obtained, the monitoring computer 36 stops the second pump 32 and calculates the pumped volume. The dosage pump 30 is now in its relatively long discharge period, while the monitoring computer 36 awaits the next suction stroke and the level detector signal occasioned thereby.

Figure 3:
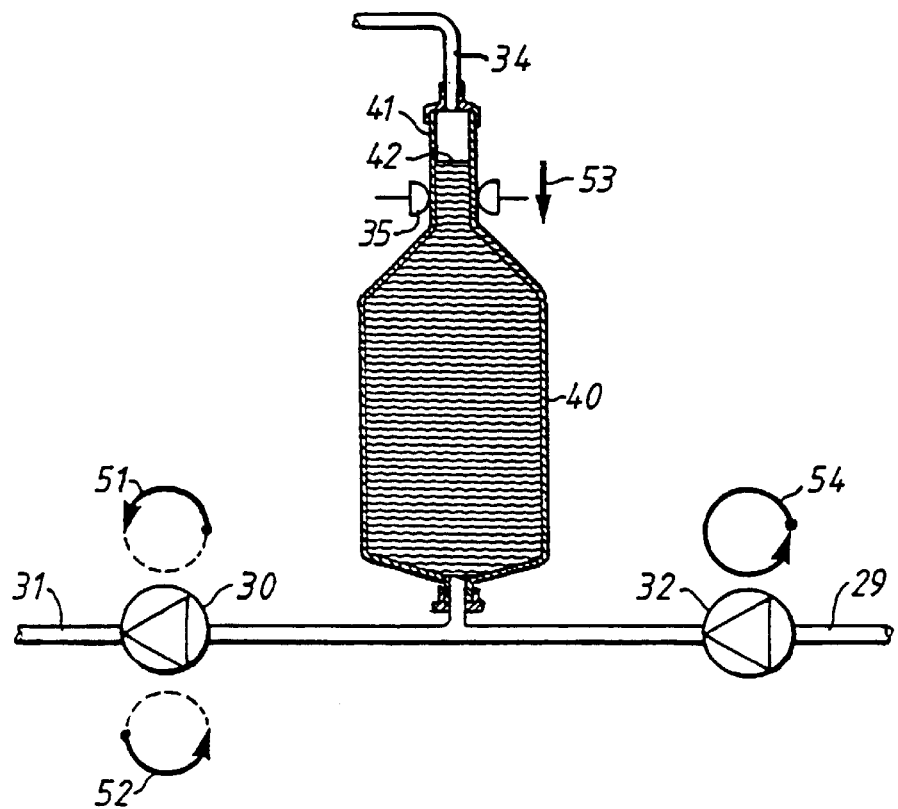
FIG. 3 is a top, elevational view of an alternative embodiment of the slave chamber of the present invention.

An alternative embodiment of the slave chamber is shown in FIG. 3. The slave chamber consists of two portions, a first lower portion 40 of large cross-section and a second upper cylindrical portion 41 of narrow cross-section, the upper end of which is connected to the ambient pressure by means of the conduit 34. The level detector 35 is positioned at the upper cylindrical narrow portion. Because of the above-mentioned hysteresis effect, the liquid level in the slave chamber, 40 and 41, is above the level detector 35 in the narrow portion, as indicated by the line 42 in FIG. 3.

During the dwell position shown in FIG. 3, liquid is continuously discharged from the dosage pump 30 to the conduit 31 while the flow to the dosage pump 30 is zero, i.e. the step motor for the dosage pump operates between 0 degrees and 180 degrees. This is indicated by the arrow 51.

When the step motor rotates past 180 degrees, the discharge becomes zero and suction of liquid to the dosage pump takes place instead, as indicated by the arrow 52. This results in the level 42 dropping in the slave chamber, 40 and 41, as indicated by the arrow 53. When the level 42 drops below the level detector 35, a signal is emitted which activates the pump 32, as indicated by the arrow 54, though with a certain time delay. When the suction stroke to the dosage pump has been completed, i.e. when the step motor rotates past 360 degrees, the flow according to the arrow 52 becomes zero and the level increases in the slave chamber, 40 and 41, until it rises above the level detector 35. Finally, a top-up of a predetermined hysteresis volume takes place, as indicated by the hatched lines in FIG. 3.

As mentioned above, the second pump 32 is activated with a certain time delay. The reason for this is that it is necessary to ensure that the dosage pump does in fact pass 360 degrees before the level once more reaches above the level detector 35. The surest way to achieve this is to ensure that the second pump 32 has a lower or substantially the same flow rate as the dosage pump and it is started a short time after the level has dropped below the level detector.

It is possible to permit the above-mentioned time delay to be so great that the second pump 32 is initially started after the dosage pump has rotated past 360 degrees, i.e. the suction stroke is completed and the discharge stroke recommences.

For reasons of safety, the lower portion 40 of the slave chamber is dimensioned so as to have a volume which is as great as, or larger than, the displacement of the dosage pump 30.

By providing for a top-up volume above the level of the level detector, several advantages are attained.

It is possible to prevent the level detector from stopping the refilling before the level actually reaches the level detector due to temporary disturbances, such as the level detector temporarily emitting a signal, for example because the inlet flow affects the level measurement. If such influenced signals arise, the last signal which was obtained is used to calculate the hysteresis volume.

In addition, it is possible to obtain a very distinct determination of the cycle time. When a suction stroke for the dosage pump commences, i.e. when the dosage pump rotates past 180 degrees, a rapid and distinct drop of the level in the slave chamber past the level detector takes place. The flow rate is greatest at the middle of the suction stroke, i.e. about 270 degrees. If the slave chamber's hysteresis volume is thus about one half the displacement of the dosage pump, a signal is obtained from the level detector when the flow velocity is greatest, thereby implying that the change-over is distinct. In addition, the second pump is inactive until such a change-over is obtained, i.e. the second pump does not interfere with the determination of the cycle time.

Since the cycle time is determined by the time between two successive signals when the level in the slave chamber drops below the level detector, the time determination becomes as accurate as possible. This is of considerable importance for the monitoring system to operate satisfactorily. An inaccuracy in the time determination is reflected in the denominator in the flow determination, which results in a non-linear function which is not easy to rectify.

In a preferred prototype of the present invention, a dosage pump of the ceramic type is used having a displacement of about 250 $\mu$l, a discharge stroke which lasts about 11 seconds and a suction stroke which lasts a few tenths of a second. A second pump of the same construction is also used. The hysteresis volume, i.e. the hatched region in FIG. 3, has a volume of about 125 $\mu$l.

Figure 4:
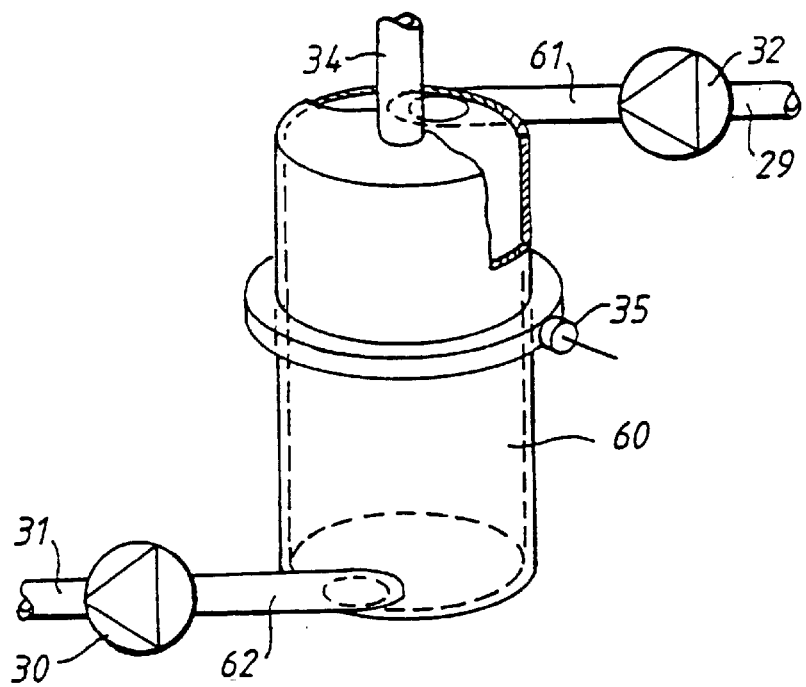
FIG. 4 is a front, elevational, partially sectional view of another embodiment of the slave chamber of the present invention.

A further alternative embodiment of the slave chamber according to the present invention is shown in FIG. 4. The slave chamber 60 has an inlet conduit 61 from the second pump 32 and an outlet conduit 62 to the dosage pump 30. At least the inlet conduit 61 is arranged tangentially. In this manner, the fluid flows in through the inlet conduit 61 over the inner surface of the slave chamber 60 along the surface and down until the fluid reaches the level of the slave chamber. By means of this arrangement of the inlet conduit, it is ensured that the level detector 35 reacts only when the level of the fluid in the chamber is above the level detector without being affected by intake of fluid through the inlet conduit.

Figure 5:
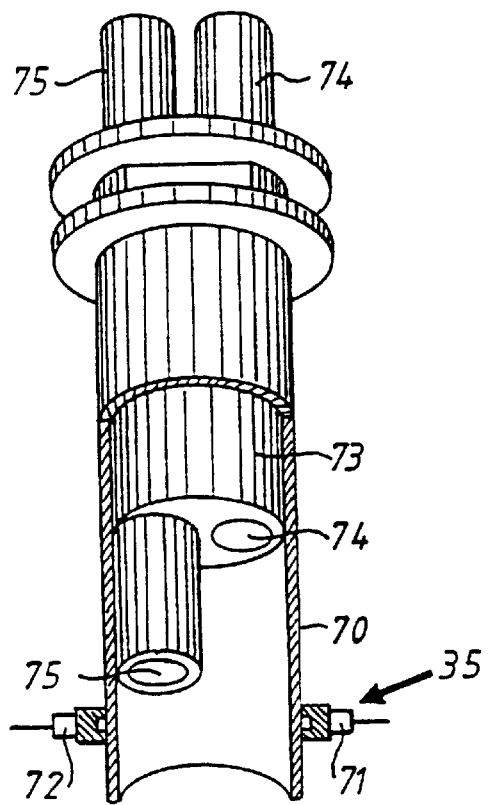
FIG. 5 is a front, elevational, partially sectional view of another embodiment of the slave chamber of the present invention.

Yet another alternative embodiment of the slave chamber is shown in FIG. 5. The slave chamber consists of a tube 70 corresponding to the chamber 60 in FIG. 4, whereby only the upper portion of the tube 70 is shown in FIG. 5. A level detector 35 is shown in the form of a transmitter 71 and a receiver 72 for infra-red radiation. An insert 73 is positioned in the tube 70. A seal (not shown in FIG. 5) is located between the upper end of the tube 70 and the insert. The insert 73 comprises a deaeration tube 74 corresponding to the conduit 34 in FIG. 1 and a feed-tube 75 which supplies liquid to the second pump. The feed-tube 75 discharges below the deaeration tube 74 and directly onto the wall of the tube 70 so that the supplied fluid runs across the wall of the tube to the liquid level in the tube 70 and thereby affects the level detector as little as possible. It is to be understood that the tube 70 and the insert 73 can be manufactured in one piece, whereby the feed-tube 75 can be chamfered so that an even better fit to the inner wall of the tube is obtained.

The deaeration conduit, 74 and 34, exhausts to the atmosphere. Alternatively, it is possible to permit the conduit, 74 and 34, to lead to some other container, for example a pressure equalization container or an expandable container.

It is possible within the scope of the present invention to use a second pump having a different construction from the concentrate dosage pump, since it is only necessary that the second pump is of the metering pump type, i.e. the flow rate has a particular relationship to the number of revolutions or partial revolutions of the drive motor.

The second pump serves to fill the slave chamber so that it is never empty and to measure the volume which is necessary to fill the chamber during each cycle. Any pump or construction which satisfies this purpose can be used as an alternative to the second pump.

The monitoring of the dosage pump takes place by means of a monitoring computer 36. According to a preferred embodiment of the present invention, the monitoring computer 36 is arranged to receive its information from the second pump. The second pump is provided with a revolution indicator which indicates when the pump shaft is at an initial position, for example 0 degrees. If the revolution indicator does not emit a signal within a predetermined time interval which is related to the filling volume of the slave chamber, an alarm signal is emitted.

In the preferred embodiment, the second pump is of the dosage pump type and is driven by a step motor. The monitoring computer 36 detects the position of the step motor and determines the volume which has been fed to the slave chamber during one cycle. By dividing the input volume by the cycle time, an estimation of the flow for the dosage pump is obtained. If this estimation lies outside of predetermined limits, an alarm signal is emitted.

A malfunction which must be taken into account is if the control arrangement partially ceases to operate. It is, for example, conceivable that it fails to refill the slave chamber while it continues to send out the last, and accepted, flow estimation to the monitoring system. In such a case, the dosage pump would pump air while the second pump's control arrangement would indicate that everything was operating as intended.

A manner in which such a malfunction can be detected is the following: The second pump has a rotation detector which emits one pulse per revolution. These pulses are normally registered by the control arrangement and a copy of the computation value is sent for each new pulse to the monitoring computer 36 of the dialysis machine. In the monitoring computer 36, the time interval between the rotation pulses is used to provide a rough flow estimation. If no pulses arrive at the monitoring computer 36, after, for example, one minute it will determine the rough estimation as zero. As long as the flow estimation sent by the control arrangement is sufficiently close, for example +20%, to the coarse flow estimation, the monitoring computer 36 will use the first mentioned estimation. Otherwise, the latter estimation is used.

The present invention has been described above with reference to preferred embodiments of the invention. The various properties and features which have been described can be combined in other ways than those which have been described in relation to the embodiments. Such modifications which are evident to a skilled person are intended to fall within the scope of the invention. The invention is limited solely by the appended claims.

What is claimed is:

1. Apparatus for monitoring the flow of a fluid through a dosage pump having a suction stroke for drawing said fluid into said dosage pump from a source of said fluid and a discharge stroke for discharging said fluid from said dosage pump, said dosage pump incorporated as an internal part of a dialysis machine to regulate the amount of a pre-prepared dialysis fluid flowing through said dialysis machine to be mixed with a concentrate fluid simultaneously being pumped through the dialysis machine, said apparatus comprising an auxiliary pump disposed between a fluid source and said dosage pump, a slave chamber disposed between said auxiliary pump and said dosage pump, said slave chamber including a level detector for detecting a first predetermined level of said fluid in said slave chamber and emitting a signal when said level of said fluid in said slave chamber is below said first predetermined level, and control means for activating said auxiliary pump after said level detector emits said signal whereby said slave chamber is refilled with said fluid by said auxiliary pump after said suction stroke of said dosage pump has drawn said fluid into said dosage pump and caused said level detector to emit said signal.

2. The apparatus of claim 1 wherein said control means is adapted to activate said auxiliary pump to refill said slave chamber to a second predetermined level above said first predetermined level of said fluid in said slave chamber.

3. The apparatus of claim 1 including regulating means for regulating said dosage pump whereby said suction stroke is carried out at a first speed and said discharge stroke is carried out at a second speed, said first speed being substantially greater than said second speed and said second speed providing a substantially constant flow rate.

4. The apparatus of claim 1 wherein said auxiliary pump includes measuring means for measuring the volume of said fluid pumped by said auxiliary pump during each cycle thereof, said control means including time measuring means for measuring the time between each cycle of said auxiliary pump and calculating means for calculating the flow of said fluid through said dosage pump based on the ratio between said volume of said fluid measured by said measuring means and said time between each of said cycles of said auxiliary pump measured by said time measuring means.

5. The apparatus of claim 1 wherein said auxiliary pump comprises a second dosage pump having a predetermined volume per cycle or portion thereof, and wherein said slave chamber includes a side wall and an outlet for said second dosage pump, said inlet being disposed adjacent to said side wall of said slave chamber.

6. A method for monitoring the flow of a fluid through a dosage pump having a suction stroke for drawing said fluid into said dosage pump from a source of said fluid and a discharge stroke for discharging said fluid from said dosage pump, said dosage pump incorporated as an internal part of a dialysis machine to regulate the amount of a pre-prepared dialysis fluid flowing through said dialysis machine to be mixed with a concentrate fluid simultaneously being pumped through the dialysis machine, an auxiliary pump disposed between said source of said fluid and said dosage pump, and a slave chamber disposed between said auxiliary pump and said dosage pump, said method comprising detecting the level of said fluid in said slave chamber and emitting a signal when said level is below a first predetermined level in said slave chamber, and actuating said auxiliary pump after emitting said signal whereby said level of said fluid in said slave chamber is increased above a second predetermined level by said discharge stroke of said dosage pump.

7. The method of claim 6 wherein said second predetermined level is greater than said first predetermined level, whereby said slave chamber is topped up with a predetermined hysteresis value above said first predetermined level.

8. The method of claim 6 including activating said auxiliary pump with a predetermined time delay after emitting said signal.

9. The method of claim 6 including regulating said dosage pump so that said suction stroke is carried out at a first speed and said discharge stroke is carried out at a second speed, said first speed being substantially greater than said second speed, and said second speed providing a substantially constant flow rate.

10. The method of claim 6 including measuring the volume of said fluid flowing through said auxiliary pump for each cycle thereof, measuring the time between each cycle of said auxiliary pump, and calculating the fluid flow through said dosage pump by determining the ratio between said measured volume of said fluid flowing through said auxiliary pump and said measured time between each cycle of said auxiliary pump.

11. Apparatus for monitoring the flow of a fluid through a dosage pump having a suction stroke for drawing said fluid into said dosage pump from a source of said fluid and a discharge stroke for discharging said fluid from said dosage pump, said apparatus comprising an auxiliary pump disposed between a fluid source and said dosage pump, a slave chamber disposed between said auxiliary pump and said dosage pump, said slave chamber including a level detector for detecting a first predetermined level of said fluid in said slave chamber and emitting a signal when said level of said fluid in said slave chamber is below said first predetermined level, control means for activating said auxiliary pump after said level detector emits said signal whereby said slave chamber is refilled with said fluid by said auxiliary pump after said suction stroke of said dosage pump has drawn said fluid into said dosage pump and caused said level detector to emit said signal, and regulating means for regulating said dosage pump whereby said suction stroke is carried out at a first speed and said discharge stroke is carried out at a second speed, said first speed being substantially greater than said second speed, and said second speed providing a substantially constant flow rate.

12. Apparatus for monitoring the flow of a fluid through a dosage pump having a suction stroke for drawing said fluid into said dosage pump from a source of said fluid and a discharge stroke for discharging said fluid from said dosage pump, said apparatus comprising an auxiliary pump disposed between a fluid source and said dosage pump, said auxiliary pump comprising a second dosage pump having a predetermined volume per cycle or portion thereof, a slave chamber disposed between said auxiliary pump and said dosage pump, said slave chamber including a level detector for detecting a first predetermined level of said fluid in said slave chamber and emitting a signal when said level of said fluid in said slave chamber is below said first predetermined level, said slave chamber further including a side wall and an inlet for said second dosage pump, said inlet being disposed adjacent to said side wall of said slave chamber, and control means for activating said auxiliary pump after said level detector emits said signal whereby said slave chamber is refilled with said fluid by said auxiliary pump after said suction stroke of said dosage pump has drawn said fluid into said dosage pump and caused said level detector to emit said signal.

13. A method for monitoring the flow of a fluid through a dosage pump having a suction stroke for drawing said fluid into said dosage pump from a source of said fluid and a discharge stroke for discharging said fluid from said dosage pump, an auxiliary pump disposed between said source of said fluid and said dosage pump, and a slave chamber disposed between said auxiliary pump and said dosage pump, said method comprising detecting the level of said fluid in said slave chamber and emitting a signal when said level is below a first predetermined level in said slave chamber, actuating said auxiliary pump after emitting said signal whereby said level of said fluid in said slave chamber is increased above a second predetermined level by said discharge stroke of said dosage pump, and regulating said dosage pump so that said suction stroke is carried out at a first speed and said discharge stroke is carried out at a second speed, said first speed being substantially greater than said second speed, and said second speed providing a substantially constant flow rate.

* * * * *